US012673973B2

(12) United States Patent
Chung et al.

(10) Patent No.: US 12,673,973 B2
(45) Date of Patent: Jul. 7, 2026

(54) PEPTIDE HAVING BLOOD COAGULATION ACTIVITY, AND USE THEREOF

(71) Applicant: CAREGEN CO, LTD., Anyang-si (KR)

(72) Inventors: Yong Ji Chung, Anyang-si (KR); Eun Mi Kim, Anyang-si (KR); Mihee Cho, Anyang-si (KR); Kyeongnan Kwon, Anyang-si (KR)

(73) Assignee: CAREGEN CO, LTD., Anyang-si (KR)

( * ) Notice: Subject to any disclaimer, the term of this patent is extended or adjusted under 35 U.S.C. 154(b) by 457 days.

(21) Appl. No.: 18/285,543

(22) PCT Filed: Apr. 8, 2022

(86) PCT No.: PCT/KR2022/005090
§ 371 (c)(1),
(2) Date: Oct. 4, 2023

(87) PCT Pub. No.: WO2022/234963
PCT Pub. Date: Nov. 10, 2022

(65) Prior Publication Data
US 2024/0368222 A1 Nov. 7, 2024

(30) Foreign Application Priority Data

May 4, 2021 (KR) ........................ 10-2021-0058155

(51) Int. Cl.
| | |
|---|---|
| *C07K 7/08* | (2006.01) |
| *A61K 33/06* | (2006.01) |
| *A61K 38/00* | (2006.01) |
| *A61K 38/10* | (2006.01) |
| *A61P 7/04* | (2006.01) |

(52) U.S. Cl.
CPC ............... *C07K 7/08* (2013.01); *A61K 33/06* (2013.01); *A61K 38/10* (2013.01); *A61P 7/04* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 11,124,540 | B2 | 9/2021 | Forssmann |
| 11,602,539 | B2 | 3/2023 | Kim et al. |
| 2006/0025524 | A1 | 2/2006 | Schneider et al. |
| 2011/0165200 | A1 | 7/2011 | Schneider et al. |
| 2016/0015855 | A1 | 1/2016 | Nohara et al. |
| 2016/0362451 | A1 | 12/2016 | Gil et al. |
| 2019/0201436 | A1 | 7/2019 | Kim et al. |
| 2019/0248920 | A1 | 8/2019 | Schmidt et al. |
| 2020/0164100 | A1 | 5/2020 | Nohara et al. |
| 2020/0247850 | A1 | 8/2020 | Forssmann |
| 2020/0399310 | A1 | 12/2020 | Gil et al. |
| 2021/0268071 | A1 | 9/2021 | Pestel et al. |
| 2022/0033442 | A1 | 2/2022 | Gil et al. |
| 2022/0089778 | A1 | 3/2022 | Schmidt et al. |

FOREIGN PATENT DOCUMENTS

| | | |
|---|---|---|
| CN | 111094320 A | 5/2020 |
| JP | 2008-508292 A1 | 3/2008 |
| JP | 2015-142720 A | 8/2015 |
| JP | 2017-510568 A | 4/2017 |
| JP | 2020-533023 A | 11/2020 |
| KR | 10-2001-0049671 A | 6/2001 |
| KR | 10-2015-0126394 A | 11/2015 |
| KR | 10-2018-0027126 A | 3/2018 |
| KR | 10-2019-0052027 A | 5/2019 |
| KR | 10-2019-0073576 A | 6/2019 |
| KR | 10-2019-0102101 A | 9/2019 |

OTHER PUBLICATIONS

International Search Report and Written Opinion of the International Searching Authority for International Patent Application No. PCT/KR2022/0050900 mailed Jul. 15, 2022 (15 pages including English Translation of ISR).
Notice of Allowance issued on Mar. 7, 2024 for the corresponding Korean patent application Application No. 10-2021-0058155 (10 pages including English Translation).
First Office Action issued on Jun. 24, 2025 for the corresponding Chinese patent application Application No. 202280031584.1 (10 pgs including English Translation).
First Office Action issued on Oct. 8, 2024 for corresponding Japanese Application No. 2023-560412 (5 pages).
Wei Shuda, et al., "Self-assembling RATEA16 peptide nanofiber designed for rapid hemostasis", Journal of Materials Chemistry B, 2020, vol. 8, No. 9, pp. 1897-1905.
Extended European Search Report dated Oct. 10, 2024 for EP Application No. 22799008.2 (9 pages).
Carter Tiffany, et al., "Self-Assembling Peptide Solution Accelerates Hemostasis", Advances in Wound Care, 2021, vol. 10, No. 4, pp. 191-203.
Huang Lu-Chieh, et al., "Bioinspired Self-assembling Peptide Hydrogel with Proteoglycan-assisted Growth Factor Delivery for Therapeutic Angiogenesis", Theranostics, 2019, vol. 9, No. 23, pp. 7072-7087.

*Primary Examiner* — Christina Bradley
(74) *Attorney, Agent, or Firm* — Merchant & Gould P.C.

(57) ABSTRACT

The present invention relates to a peptide, of a novel sequence, characterized by being gelled in accordance with the pH condition. Since the peptide may induce blood coagulation, a composition comprising the peptide can be utilized for the use of inducing hemostasis.

11 Claims, 7 Drawing Sheets

Specification includes a Sequence Listing.

【Figure 1】
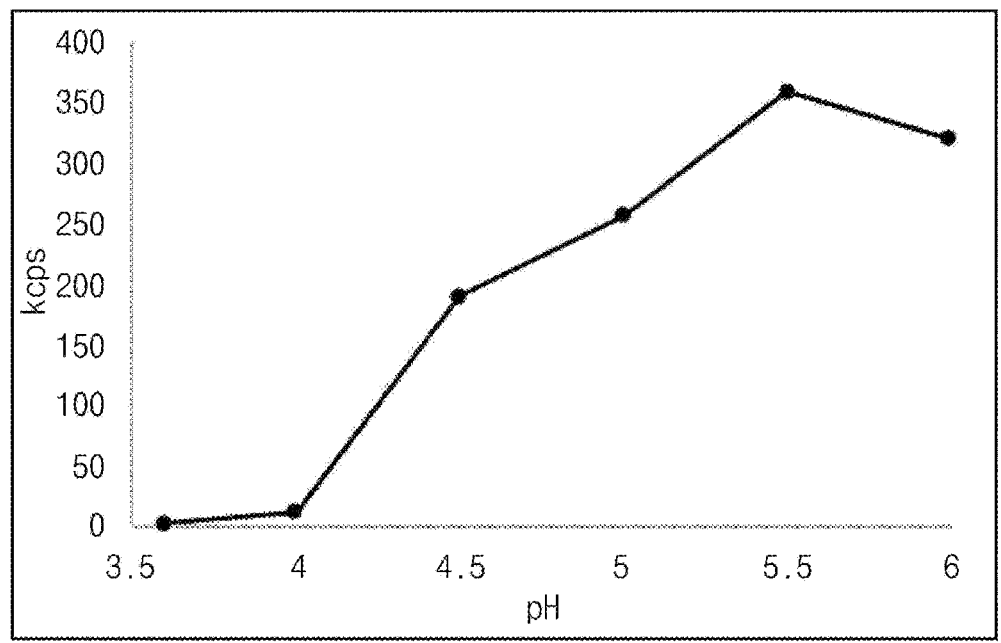
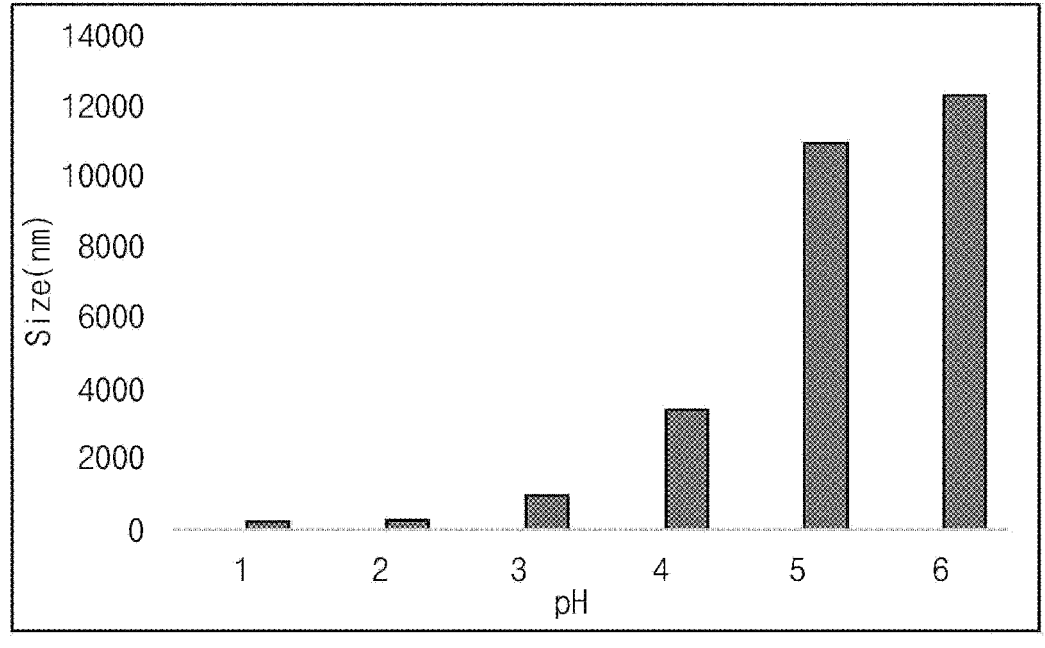

【Figure 2】
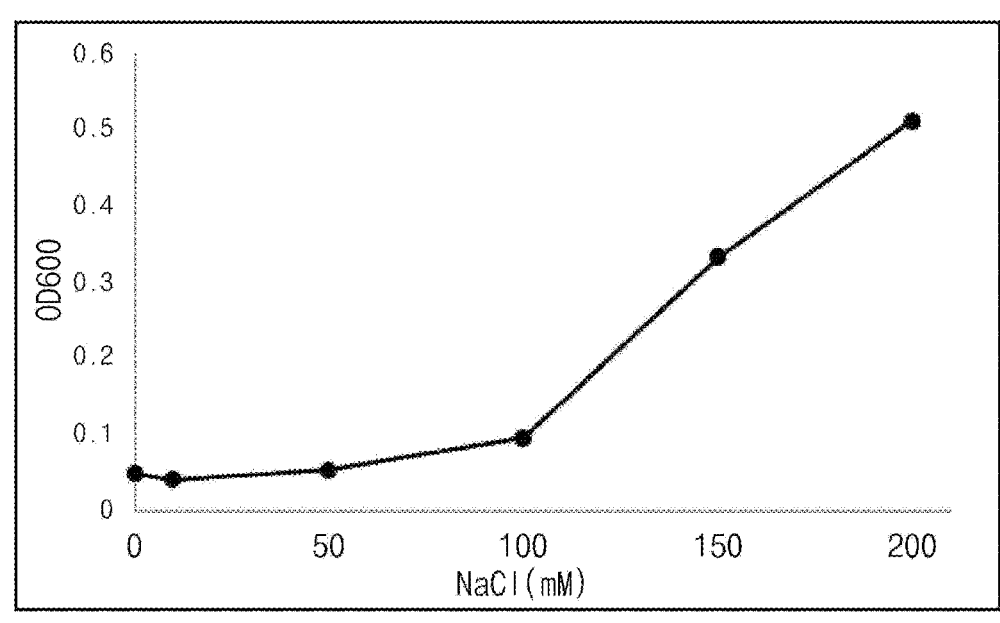
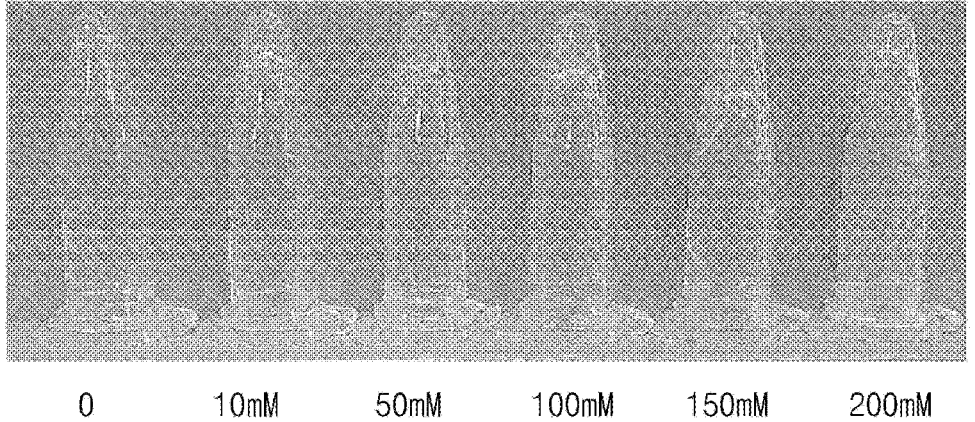

【Figure 3】
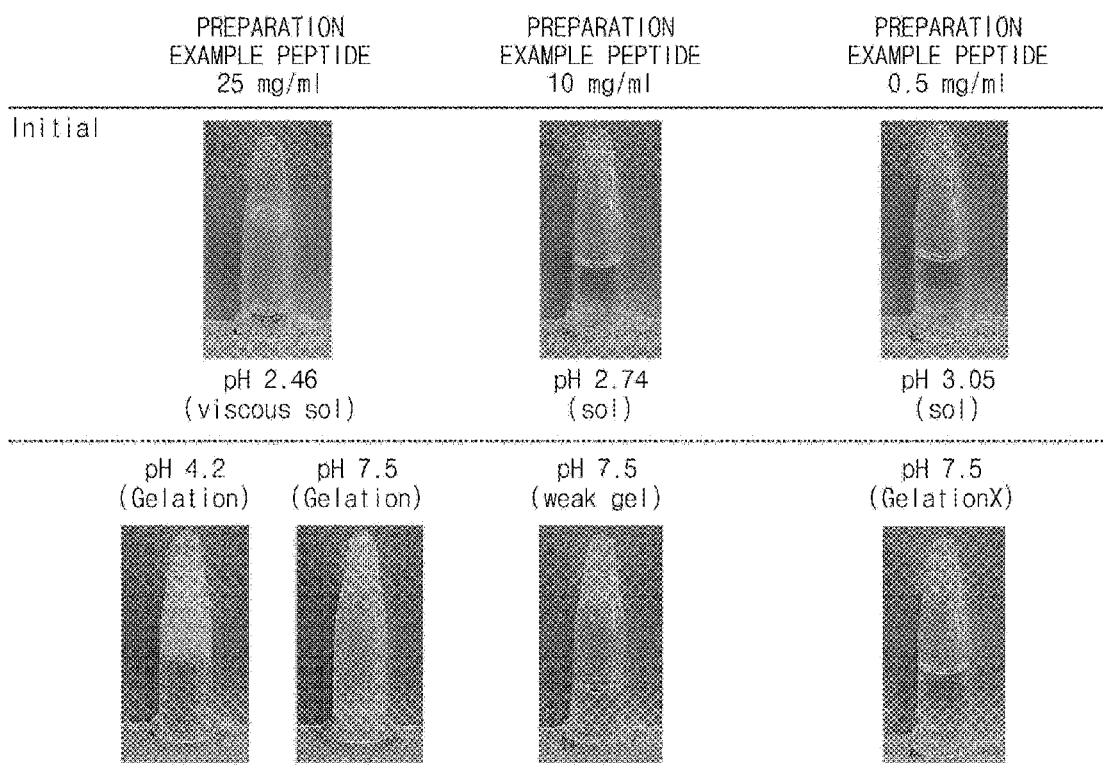
【Figure 4】
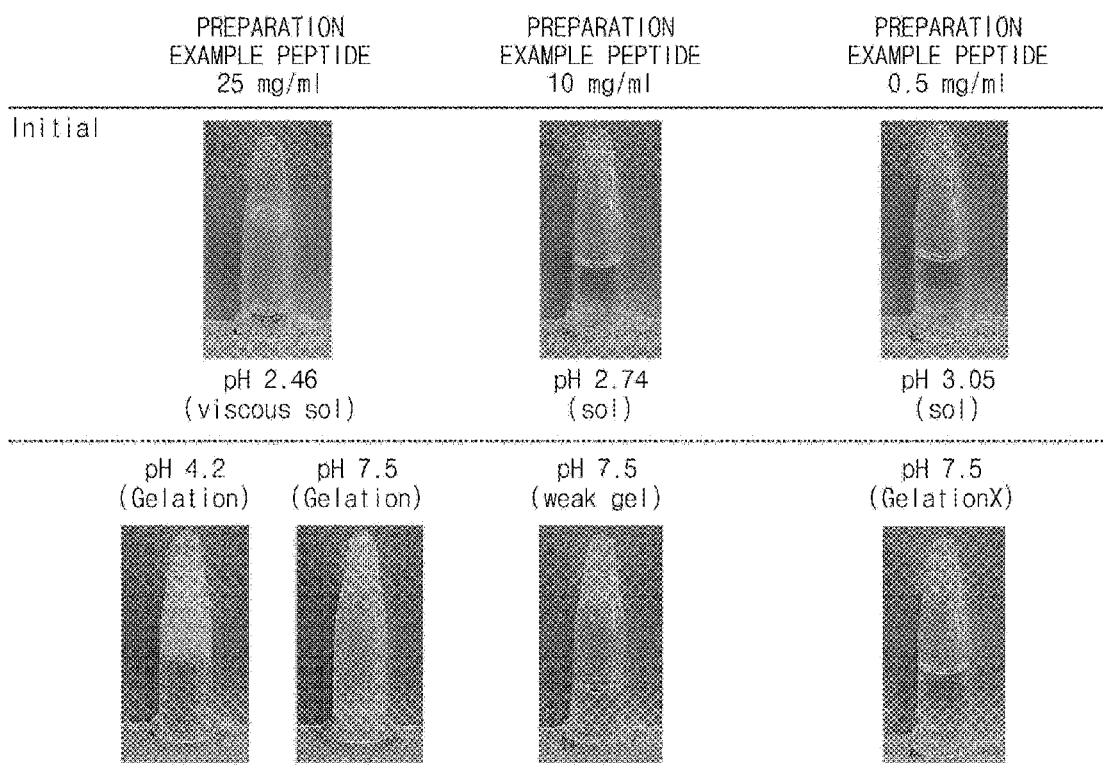
Final concentration (ug/mL)
|  | 1,000 | 500 | 250 | 125 | 62.5 | 0 |
|---|---|---|---|---|---|---|
| PREPARATION EXAMPLE PEPTIDE-TREATED GROUP #1 | | | | | | |
| PREPARATION EXAMPLE PEPTIDE-TREATED GROUP #2 | | | | | | |
| RADA16 PEPTIDE-TREATED GROUP | | | | | | |

【Figure 5】
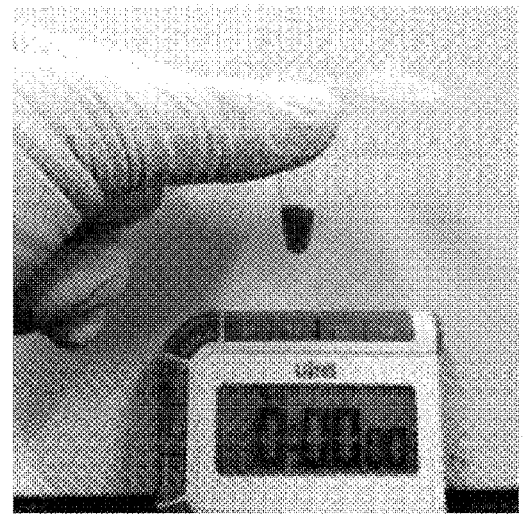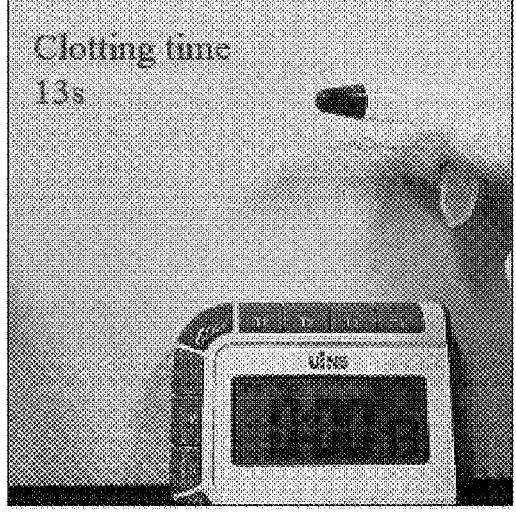
【Figure 6】
Coagulation test
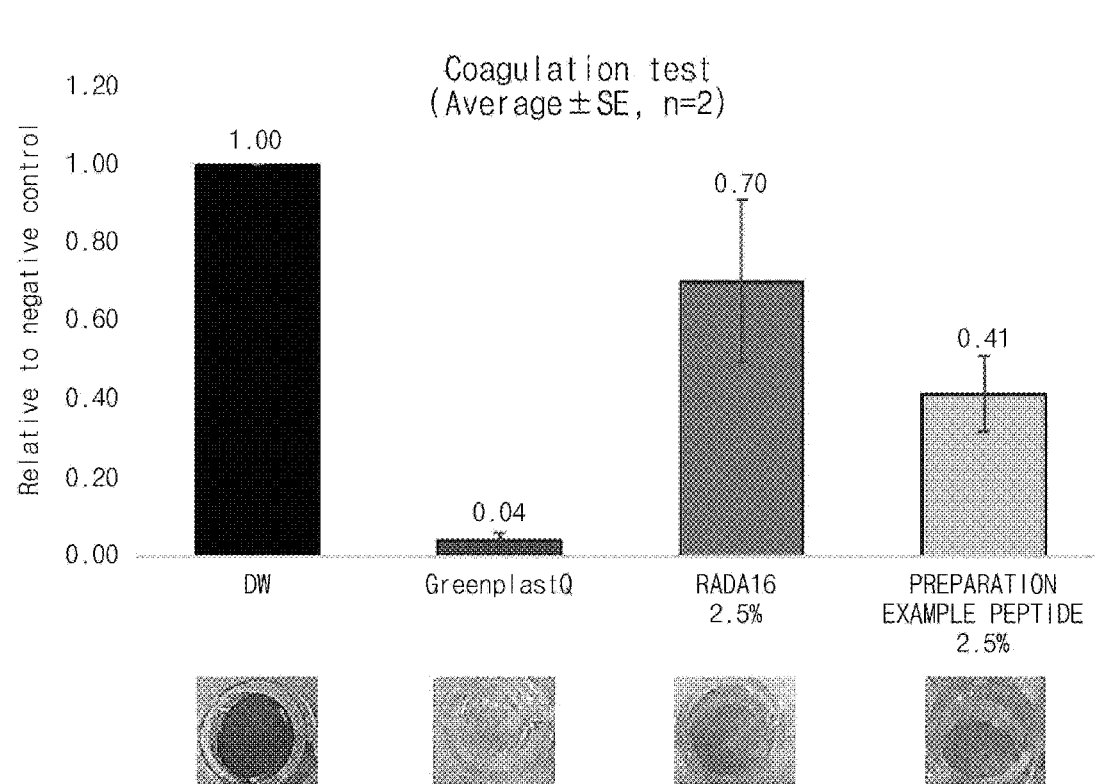

Figure 7

【Figure 8】
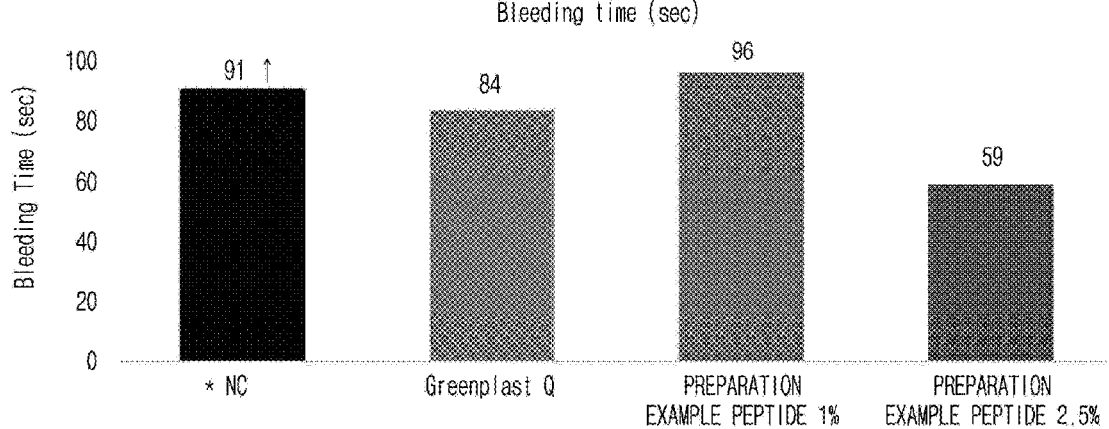
【Figure 9】
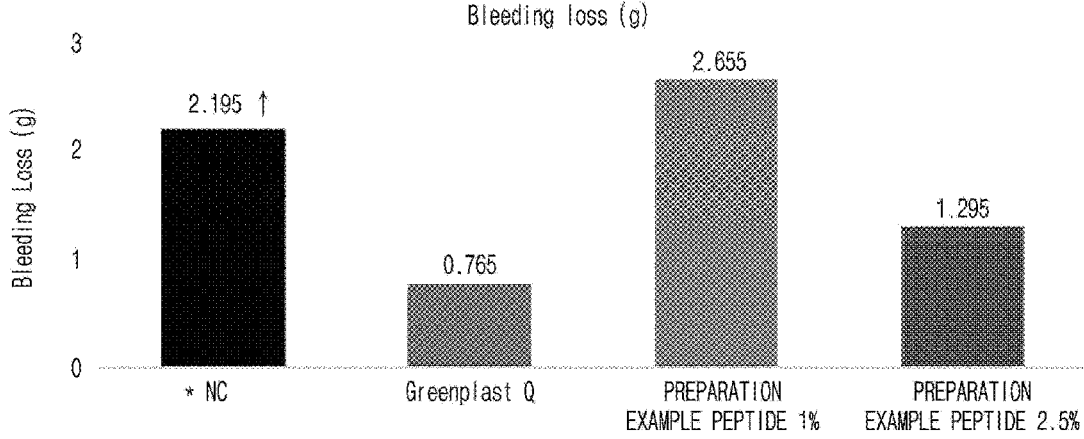

【Figure 10】
Hemolysis test
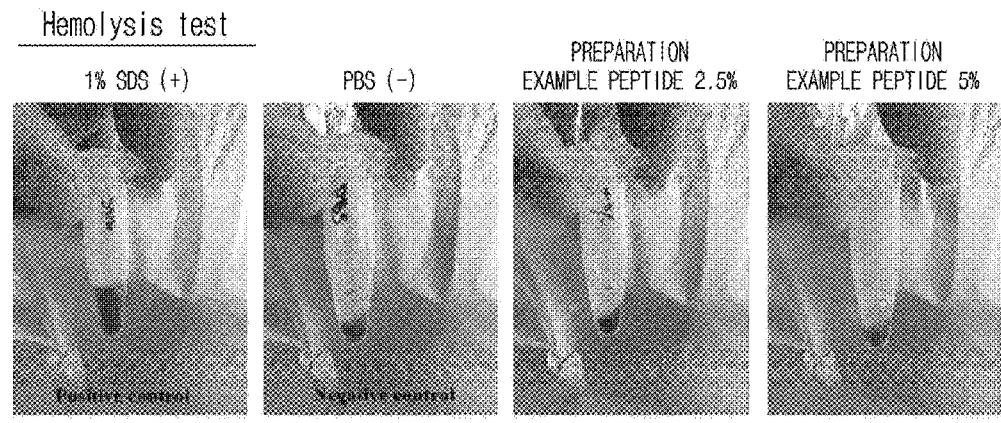
| 1% SDS (+) | PBS (−) | PREPARATION EXAMPLE PEPTIDE 2.5% | PREPARATION EXAMPLE PEPTIDE 5% |
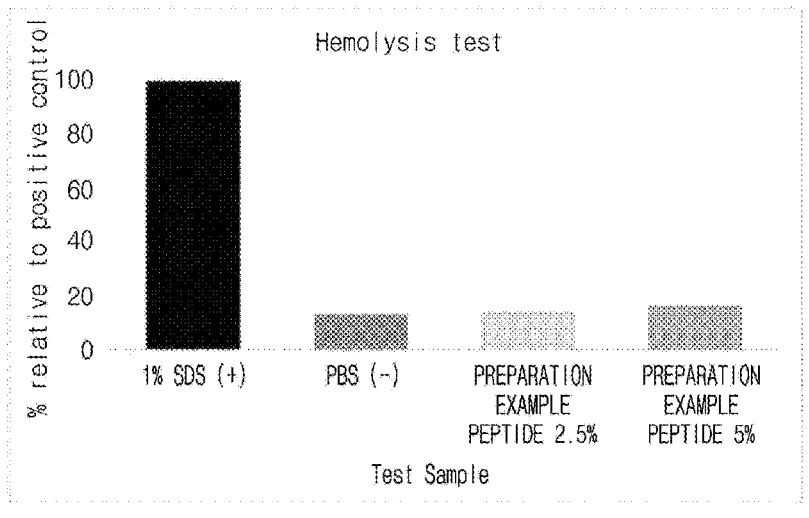

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: synthetic

<400> SEQUENCE: 1

Ser Ala Ser Gln Ala Tyr Leu Ala Gly Asn Ile Thr
1               5                   10
```

PEPTIDE HAVING BLOOD COAGULATION ACTIVITY, AND USE THEREOF

CROSS-REFERENCE TO RELATED APPLICATIONS

This application is a National Stage Application of PCT/KR2022/005090, filed 8 Apr. 2022, which claims benefit of Serial No. 10-2021-0058155, filed 4 May 2021 in Republic of Korea and which applications are incorporated herein by reference. To the extent appropriate, a claim of priority is made to each of the above disclosed applications.

SEQUENCE STATEMENT

This application contains a Sequence Listing, which has been submitted electronically in ASCII format and is hereby incorporated by reference in its entirety. Said ASCII copy, created and filed in PCT/KR2022/005090, is named 2021OPA6441_ST25.txt and is 467 bytes (4.00 KB) in size.

TECHNICAL FIELD

The present invention relates to a novel peptide capable of inducing blood coagulation and a use thereof.

BACKGROUND ART

The vascular system plays an important role in transporting various nutrients and transporting oxygen and carbon dioxide in animals, and blood and body fluids are exchanged between blood vessels and tissues. However, if damage to skin tissue or blood vessels occurs, blood and body fluids may leak out. If such bleeding is excessive, oxygen delivery is not normally performed, which can lead to death. Therefore, hemostasis methods to reduce bleeding have been developed.

In the living body, there is a system that induces coagulation of blood by itself. Hemostasis can occur by inhibiting the outflow of blood or body fluid components while blood clots or blood clots are formed by aggregation of blood cells by thrombin formed through an enzymatic reaction and fibrin fibers produced therefrom. However, if excessive bleeding occurs due to the occurrence of deep and large wounds, hemostasis may not be sufficient with only the coagulation system of the living body, and there is also a great need to control excessive bleeding that inevitably accompanies surgical operations. Therefore, it can be said that the demand for a method for effective hemostasis and a substance having hemostasis activity is always high.

Chitosan, collagen, starch, beeswax and the like have been used as components of conventional products used for the purpose of hemostasis, and they are manufactured and applied in the form of powder, sponge, sheet, gel and the like. In Korean Laid-open Patent Publication No. 2018-0027126, a hemostasis effect was induced using a composition containing a crosslinked hyaluronic acid derivative matrix.

However, preparations for hemostasis should be harmless to the living body in that they are basically applied to damaged or injured areas and should not cause side effects such as hemolysis. Hemostasis products using chitosan, polymers, etc., which have been developed as conventional medical devices, have insignificant hemostasis efficacy, and there is a problem in that residues must be decomposed or discharged from the body after application to the living body, and inflammatory reactions may be induced by the residues. In addition, in the case of a conventional biological drug preparation having a blood coagulation mechanism, there is a disadvantage in that it is not easy to manufacture and transport/storage because it is a biologically derived component. It also has the disadvantage of poor usability because it requires a long time to apply, such as requiring a thawing process before use or using it after mixing a first agent and a second agent. Therefore, it is necessary to develop a peptide preparation for promoting blood coagulation synthesized using an amino acid component, which is a biological component, while having excellent manufacturing and storage stability and hemostasis efficacy.

DISCLOSURE

Technical Problem

An object of the present invention is to provide a peptide that can be gelated under specific conditions and used to induce blood coagulation.

In addition, an object of the present invention is to provide a composition capable of effectively inducing hemostasis using the peptide.

In addition, an object of the present invention is to provide a method for hemostasis using the composition.

Technical Solution

In order to achieve the above object, one aspect of the present invention provides a peptide having pH-dependent gelation property, which comprises the amino acid sequence of SEQ ID NO: 1.

Another aspect of the present invention provides a composition for inducing hemostasis comprising the peptide.

Still another aspect of the present invention provides a method for hemostasis comprising the step of treating the composition to a bleeding site of an animal in which bleeding occurs.

Advantageous Effects

The peptide provided in the present invention has the property of self-gelation under neutral pH conditions. Specifically, the peptide can gelate under a specific pH condition to form an aggregate, and accordingly, when blood or a body fluid is treated with the peptide or a composition containing the same, gelation of the peptide can proceed depending on the pH condition in the blood. The peptide aggregates with blood cells or the nanofibrous structure formed by gelation of the peptide surrounds and traps blood cells and blood components other than blood cells to form a lump. Accordingly, there is an effect of inducing hemostasis by precipitating or obstructing the flow or outflow of blood.

The peptide of the present invention and the composition comprising the same have an activity of inducing blood coagulation at a level similar to that of conventional hemostasis agents, have an excellent effect of shortening the hemostasis time, and do not induce hemolysis, so they can be usefully used for inducing hemostasis.

In particular, under acidic conditions, gelation does not proceed and may be in the form of a liquid or sol. Therefore, as the peptide of the present invention and composition maintains an acidic pH condition before being applied to actual blood or body fluid, it may exhibit properties more suitable for storage or application due to fluidity. In addition, when applied to blood or body fluids, gelation proceeds according to its neutral pH, which has the advantage of efficiently exhibiting hemostasis at the actual bleeding site.

In addition, the peptide of the present invention and the composition comprising the same are prepared as an amino acid component constituting a living body. Therefore, when applied to the living body, there is an advantage that side effects or problems of decomposition/discharge are less likely to occur, and thus the possibility of inflammatory reactions is low. In addition, compared to conventional preparations for hemostasis, it is easy to manufacture and has excellent storage stability.

However, the effects of the present invention are not limited to the effects mentioned above, and other effects not mentioned will be clearly understood by those skilled in the art from the following description.

DESCRIPTION OF DRAWINGS

FIG. 1 is a graph illustrating the measured light scattering intensity kcps value and particle size of the peptide of the present invention according to pH change.

FIG. 2 is a graph illustrating the measured optical density value (OD 600) of the solution containing the peptide of the present invention according to the change in salt (NaCl) concentration, and a photograph illustrating the form of the solution according to the salt concentration.

FIG. 3 is a photograph illustrating the difference in the degree of gelation according to the difference in the concentration of the peptide of the present invention.

FIG. 4 is the result of the hemagglutination test observed by mixing the composition containing the peptide of the present invention with the red blood cell suspension collected from mice by concentration. The area marked with a circle represents the experimental result of the concentration at which blood cells did not precipitate and started to form clots.

FIG. 5 is a photograph illustrating that blood coagulation occurred after 13 seconds as a result of performing a blood coagulation test using a composition containing the peptide of the present invention.

FIG. 6 is a result of performing a blood coagulation test using the composition containing the peptide of the present invention, and is a result of measuring and comparing the optical density of the supernatant of the centrifuged sample. Relative values were illustrated based on the values of the negative control group (DW) treated with distilled water, and the group treated with Greenplast (GreenplastQ) and RADA16 peptide preparations was used as the control group.

FIG. 7 is the result of animal experiments on the hemostasis effect of the composition containing the peptide of the present invention, and illustrates pictures of the bleeding site, amount of blood loss, and bleeding time values of the control group not treated with anything (No Treatment), the control group treated with Greenplast (Greenplast Q), and the groups treated with the peptide of the present invention at concentrations of 1% and 2.5%, respectively. In the case of the control group not treated with anything, the amount of blood loss was measured 90 seconds after the start of bleeding.

FIG. 8 is a graph illustrating the results of animal experiments on the hemostasis effect of the composition containing the peptide of the present invention. The graph illustrates a comparison of the bleeding time values of the control group (NC) not treated with anything, the control group treated with Greenplast (Greenplast Q), and the group treated with the peptide of the present invention at concentrations of 1% and 2.5%, respectively. In the case of the control group not treated with anything, the experiment was stopped about 90 seconds after the start of bleeding.

FIG. 9 is a graph illustrating the results of animal experiments on the hemostasis effect of the composition containing the peptide of the present invention. The graph illustrates the comparison of blood loss values of the control group (NC) not treated with anything, the control group treated with Greenplast (Greenplast Q), and the group treated with the peptide of the present invention at concentrations of 1% and 2.5%, respectively. In the case of the control group not treated with anything, the amount of blood loss was measured 90 seconds after the start of bleeding.

FIG. 10 is a photograph and a graph illustrating the comparison of hemolysis test results using a composition containing the peptide of the present invention. As a control, 1% SDS and PBS were treated instead of the composition of the present invention, and the result was confirmed.

BEST MODE

Hereinafter, the present invention will be described in detail.

1. Peptides With pH-Dependent Gelation Property

One aspect of the present invention provides a novel peptide having pH-dependent gelation property.

In the present invention, the term "peptide" refers to a polymer composed of two or more amino acids linked by peptide bonds.

In the present invention, the term "gelation" refers to a phenomenon of changing into a gel form (shape), and means that colloidal particles in a solution lose fluidity and have a certain form in a solid or semi-solid state. In general, a gel may be gelated while forming a chemical bond in a sol in which solid particles are dispersed in a liquid.

The peptide includes the amino acid sequence of SEQ ID NO: 1. The peptide may include a mutant peptide having a different sequence by deletion, insertion and substitution of amino acid residues, or a combination thereof within a range that does not affect the properties or activity of the peptide, or may be in the form of a protein fragment having the same function. Amino acid modifications at the protein and peptide level that do not entirely alter the properties or activity of the inclusion of the amino acid sequence of SEQ ID NO: 1 are known in the art. In some cases, the modification may be carried out by phosphorylation, sulfation, acrylation, glycosylation, methylation, farnesylation, and the like. Accordingly, the peptide includes not only the amino acid sequence of SEQ ID NO: 1 but also a peptide having an amino acid sequence substantially identical thereto or a variant thereof. The peptide having the substantially identical amino acid sequence may be a peptide including an amino acid sequence having homology of at least 90%, at least 91%, at least 92%, at least 93%, at least 94%, at least 95%, at least 96%, at least 97%, at least 98%, at least 99%, or at least 99.5% with the amino acid sequence of SEQ ID NO: 1, but is not limited thereto. Any peptide containing a sequence having at least 90% amino acid sequence homology with the amino acid sequence of SEQ ID NO: 1 and having the same activity is included in the scope of the present invention.

The peptide of the present invention includes the amino acid sequence of SEQ ID NO: 1 and may be composed of 20 or less amino acids exhibiting gelation characteristics in a pH-dependent manner. Specifically, the peptide may consist of 20 or less, 18 or less, 15 or less, or 12 amino acids.

In addition, the peptide of the present invention can be obtained by various methods widely well known in the art. As an example, it may be produced using polynucleotide recombination and a protein expression system, or in vitro synthesis through chemical synthesis such as peptide synthesis, and cell-free protein synthesis, but is not limited by its production method.

In addition, in order to obtain better chemical stability, enhanced pharmacological properties (half-life, absorption, potency, efficacy, etc.), altered specificity (e.g., broad biological activity spectrum), reduced antigenicity, a protecting group may be bound to the N-terminus or C-terminus of the peptide. For example, the protecting group may be an acetyl group, a fluorenyl methoxy carbonyl group, a formyl group, a palmitoyl group, a myristyl group, a stearyl group or polyethylene glycol (PEG), but any component capable of modifying the peptide, particularly enhancing the stability of the peptide, may be included without limitation. The 'stability' refers to storage stability (e.g., storage stability at room temperature) as well as in vivo stability that protects the peptide of the present invention from attack by proteolytic enzymes in vivo.

The peptide of the present invention may be one gelated at neutral pH. Specifically, the peptide may be gelated under pH conditions ranging from pH 4 to pH 8, pH 4 to pH 7, pH 4.5 to pH 7 or pH 5 to pH 7, but is not limited thereto. The peptide may be gelated in a pH range that can be exhibited by blood or body fluids of humans or animals other than humans.

In addition, the peptide of the present invention may show a sol or liquid form at acidic pH. Specifically, the solution containing the peptide may be in the form of a sol or liquid at an acidic pH, for example, in the range of pH 0 to pH 3.9. The peptide of the present invention may have the property of gelation to lose fluidity and form a solid or semi-solid gel as the pH is changed and given a neutral pH condition.

In a specific embodiment of the present invention, the light scattering intensity kcps value and size of the peptide were measured while changing the pH, and it was confirmed that gelation proceeded by confirming that the size of the particles in the solution increased and the kcps value gradually increased under the condition of pH 4 or higher. In particular, peptide aggregation was observed with the naked eye under conditions of pH 6 or higher. Therefore, it was confirmed that the peptide of the present invention has gelation properties in a pH-dependent manner, more specifically, under neutral pH conditions.

The peptide may have a property of gelation in the presence of a salt, and for example, the salt may be sodium chloride (NaCl), but is not limited thereto. The peptide may be gelated under conditions where the salt concentration is 50 mM or more, 60 mM or more, 70 mM or more, or 100 mM or more, and the degree of gelation may increase as the salt concentration increases. The peptide may be gelated within a salt concentration range that blood or body fluids of humans or animals other than humans can exhibit.

In a specific embodiment of the present invention, the degree of aggregation of the peptide was visually confirmed by measuring the optical density while changing the salt concentration. As a result, it was confirmed that turbidity gradually increased and gelation occurred due to an increase in viscosity when the concentration of sodium chloride (NaCl) was 100 mM or more.

According to the properties of the peptide as described above, the peptide can induce blood coagulation. The blood coagulation means blood hardening, and the peptide can induce a reaction in which liquid blood is solidified into solid thrombus and blood clots. More specifically, since the peptide has a property of gelation, the nanofibrous structure formed due to the gelation of the peptide surrounds blood cells and other blood components in the blood and induces aggregation. Blood cells aggregated together with the peptide of the present invention may form clumps, which may increase in volume and precipitate or obstruct blood flow and outflow. Therefore, since the peptide of the present invention has an activity capable of inducing blood coagulation when bleeding occurs, the peptide of the present invention or a composition containing the same can be usefully used for hemostasis.

2. Composition for Inducing Hemostasis and Hemostasis Method Using the Same

Another aspect of the present invention provides a composition for inducing hemostasis containing the peptide.

The peptide includes the amino acid sequence of SEQ ID NO: 1, and the description thereof is the same as the description of the peptide in item '1. Peptides with pH-dependent gelation property', so the specific description is incorporated therein.

In the present invention, the term 'hemostasis' refers to reduce bleeding, which may mean both reducing the outflow of blood as well as the outflow of body fluids other than blood. In addition, the hemostasis is a concept that includes all of inducing or promoting coagulation of blood or body fluids, reducing the amount of blood loss, reducing the bleeding time, stopping bleeding, promoting the formation of thrombi or blood clots, and the like.

The peptide of the present invention is characterized by gelation in a pH-dependent manner. Therefore, a composition containing the peptide can also be aggregated and gelated according to pH conditions, and can be used for inducing hemostasis as it aggregates with blood cells. Specifically, gelation of the peptides included in the composition may occur at the site of bleeding, and the formed gel or nanofibers may aggregate while surrounding blood cells and other blood components. Aggregates formed in this way may precipitate in large lumps or obstruct the flow or outflow of blood. Therefore, the composition of the present invention can be usefully used to induce hemostasis at the bleeding site.

The composition may exhibit an acidic pH. For example, the composition may have a pH range of 0 to 3.9, and thus may be in the form of a liquid or sol in which gelation is not performed.

The peptide may be included in the composition at a concentration of 0.5 mg/ml to 50 mg/ml. Specifically, the peptide may be included at a concentration of 0.5 mg/ml to 50 mg/ml, 1 mg/ml to 40 mg/ml, 10 mg/ml to 35 mg/ml or 20 mg/ml to 30 mg/ml, but is not limited thereto. When the concentration of the peptide included in the composition of the present invention is within the above range, gelation by the peptide can sufficiently occur, thereby inducing blood coagulation and sufficiently exhibiting the hemostasis effect.

The composition may further include calcium ions. The calcium ion may be added to the composition of the present invention, for example in the form of calcium chloride (CaCl$_2$). Calcium ions are known to induce and accelerate the blood coagulation reaction in the blood, and more specifically, they can help the thrombin formation reaction by enzymes such as thrombokinase involved in the blood coagulation reaction. Therefore, the calcium ion may help the blood coagulation or hemostasis effect of the composition of the present invention, and may also be included to form an appropriate salt concentration.

The composition may coagulate blood at neutral pH. More specifically, it may be capable of coagulating blood under pH conditions ranging from pH 4 to pH 8, pH 4 to pH 7, pH 4.5 to pH 7 or pH 5 to pH 7, but is not limited thereto. The composition may coagulate blood in a pH range that can be exhibited by blood or body fluids of humans or animals other than humans.

The composition may coagulate blood under the condition that the salt concentration is 50 mM or more. More specifically, it may be capable of coagulating blood under the condition that the salt concentration is 50 mM or more, 60 mM or more, 70 mM or more or 100 mM or more, but is not limited thereto. The composition may coagulate blood in a salt concentration range that can be exhibited by blood or body fluids of humans or animals other than humans.

The composition may not cause hemolysis. The hemolysis phenomenon means a phenomenon in which blood cells are destroyed, and may specifically be a phenomenon in which red blood cells are destroyed. Since the composition of the present invention does not cause hemolysis, it is suitable for application to blood or bleeding sites.

In a specific embodiment of the present invention, red blood cells isolated from blood collected from mice were treated with the composition of the present invention, and then centrifuged to measure the optical density of the supernatant. As a result, the measured value was significantly smaller than that when 1% SDS was treated. This is the result of not causing hemolysis of red blood cells, and it was confirmed that the composition of the present invention does not induce hemolysis of blood.

The composition can be made into various types of preparations to induce hemostasis. Specifically, the composition may be in at least one form selected from the group consisting of powder formulations, patches, gauze, sprays and injections, but is not limited thereto. Specifically, the composition may be in at least one form selected from the group consisting of powder formulations, patches, gauze, sprays and injections, but is not limited thereto.

Another aspect of the present invention provides a method for hemostasis using the composition.

The hemostasis method of the present invention includes the step of treating the composition of claim 4 to a bleeding site of an animal in which bleeding occurs. The animals include both humans and non-human animals, and the non-human animals include, for example, cows, pigs, sheep, goats, deer, horses, rats, or poultry (chicken, duck, goose, turkey, ostrich, turkey, pheasant), but is not limited thereto, and can be applied without limitation to any animal having a vascular system.

The bleeding site includes all sites where blood or body fluid other than blood leaks out. For example, it may include all areas where blood or body fluid leaks due to damage to the surface of the skin, areas where blood leaks due to damage or cut to blood vessels, and intestinal bleeding areas.

The method of treating the composition may vary depending on the form of the composition. For example, if the composition is a powder formulation, spray, etc., it can be treated by spraying or applying to the bleeding area, and if it is a patch, gauze, etc., it can be treated by attaching to the surface of the bleeding area. In addition, if the composition is an injection, it may be treated by injecting the bleeding site using a syringe, but is not limited thereto.

The hemostasis method may further include the step of applying physical pressure to the bleeding site after the step of treating the composition. However, the hemostasis method of the present invention is not limited thereto, and any hemostasis method commonly used to suppress s bleeding may be applied together with the step of treating the composition of the present invention without limitation.

Hereinafter, the present invention will be described in detail by Examples.

However, the following Examples specifically illustrate the present invention, and the content of the present invention is not limited by the following Examples.

Preparation Example

Preparation of Peptide

A peptide having the amino acid sequence of SEQ ID NO: 1 described in Table 1 below was synthesized using an automatic peptide synthesizer (Milligen 9050, Millipore, USA), and then the synthesized peptides were purified using C18 reverse phase high performance liquid chromatography (HPLC) (Waters Associates, USA). ACQUITY UPLC BEH300 C18 (2.1 mm x 100 mm, 1.7 μm, Waters Co, USA) was used as the column.

TABLE 1

| SEQ ID NO: | Peptide Sequence |
| --- | --- |
| 1 | SASQAYLAGNIT |

Experimental Example 1

Confirmation of Peptide Gelation According to pH Change

In order to confirm the gelation phenomenon of the peptide of the present invention having the amino acid sequence of SEQ ID NO: 1, the change in the degree of gelation was confirmed by measuring the change in physical properties of the peptide of the present invention while adjusting the pH. Specifically, the peptide of the present invention was dissolved at a concentration of 1 mg/ml using 10 mM acetate buffer (pH 3.4 to pH 5.5) and 10 mM phosphate buffer (pH 6.0 to pH 7.4). And when the pH was 3.4, 4, 4.5, 5, 5.5, 6, 6.5, 7 and 7.4, respectively, the size and light scattering intensity (unit:kcps) of the peptides were measured using a light scattering analyzer (ZetaSizer, Malvern panalytical, UK).

As a result, as can be seen in FIG. 1, at pH 3.4 and 4, the change in the kcps value of light scattering intensity was not large, but when the pH was increased to 4.5, it was measured that the kcps value increased significantly. Therefore, it was confirmed that the gelation point, which is the pH at which gelation of the peptide of the present invention starts, is between pH 4 and pH 4.5. And as the pH gradually increased, the kcps value also gradually increased, and the highest value was measured at pH 5.5. It is expected that this is because the peptide of the present invention induces a structural change as the pH increases, and the resulting arrangement of the particles results in a gelation property. Even at pH 6, the kcps value of the peptide was maintained high, and it was visually confirmed that peptide aggregation occurred. As the pH increased, the size of the particles gradually increased, confirming that peptide aggregation and gelation occurred at neutral pH.

Through the above results, it can be confirmed that the peptide has the characteristic that gelation does not proceed under acidic pH conditions, so no aggregation phenomenon is observed, but gelation begins when the pH gradually increases to pH 4 to 4.5, and when it reaches neutral pH, it aggregates to form a gel. Therefore, the peptide can form aggregates depending on its pH conditions, and there is a possibility that it can be used for inducing coagulation of blood. In particular, considering the characteristics of the peptide of the present invention, in which gelation occurs in a pH range similar to blood and body fluids of animals, it was confirmed that it is suitable for application to the living body.

Experimental Example 2

Confirmation of Peptide Gelation According to Salt Concentration

In addition to confirming that the peptide of the present invention has a gelation characteristic with an increase in pH according to Experimental Example 1, it was also confirmed how the gelation of the peptide changes according to the concentration of a salt such as NaCl. Specifically, 0, 10, 50, 100, 150, and 200 mM NaCl aqueous solutions were prepared, and 25 mg/ml of the peptide of the present invention having the amino acid sequence of SEQ ID NO: 1 was added to 200 μl of the NaCl aqueous solution, respectively, followed by vortexing at 3,500 rpm for mixing. And the optical density of the mixture of the peptide and salt solution was measured at a wavelength of 600 nm.

As a result, as can be seen in FIG. 2, the turbidity of the mixture began to increase when the concentration of NaCl was 100 mM, and the turbidity of the mixture continued to increase until the concentration of NaCl reached 200 mM. This is expected to be due to the promotion of aggregation as the interaction between the molecules of the peptide of the present invention increases. In addition, it was confirmed that the viscosity tended to increase up to the NaCl 150 mM concentration.

Since a certain amount of salt is dissolved in animal blood or body fluid, it is necessary to check whether gelation of the peptide of the present invention sufficiently occurs even in an environment similar to blood or body fluid. As a result of gelation of the peptide according to the concentration of NaCl, it was confirmed that the peptide of the present invention can be usefully used for inducing coagulation of blood by forming a gel phase in an in vivo environment.

Experimental Example 3

Confirmation of Peptide Gelation According to Peptide Concentration

Depending on the concentration of the peptide of the present invention having the amino acid sequence of SEQ ID NO: 1, it was confirmed how the gelation degree of the peptide changes. Specifically, the peptides were mixed with distilled water at concentrations of 5, 10 and 25 mg/ml, respectively, and dissolved in a 1.5 ml microtube. The phase transition of the mixture containing the peptide was visually observed while the pH was gradually increased by adding 5 N NaOH thereto.

As a result, as can be seen in FIG. 3, the peptide of the present invention mostly showed a sol phase in the first acidic pH condition, but gelation progressed as the pH increased. When the concentration of the peptide was 0.5 mg/ml, gelation did not occur even when the pH reached 7.5, but as the concentration of the peptide increased, the gelation of the peptide was further promoted. It was confirmed that gelation proceeded from the pH 4.2 condition in the tube containing the peptide at a concentration of 25 mg/ml.

Experimental Example 4

Confirmation of Hemagglutination Effect of Peptide of the Present Invention (Hemagglutination Assay)

Using the peptide of the Preparation Example, which was confirmed to have gelation and aggregation properties under neutral pH conditions, it was confirmed whether there was an aggregation effect on red blood cells in blood. Specifically, the blood collected from the rat was dispensed into a 1.5 ml EP tube, centrifuged at 1,500 g for 10 minutes, then the upper layer of plasma was removed and washed three times with 0.9% aqueous sodium chloride solution. Red blood cells and sodium chloride aqueous solution were mixed in a ratio of 3:11 (v/v) to prepare a red blood cell suspension. As a control for the peptide of the present invention, a commercially available RADA16 peptide sample (3D Matrix) for research known to have hemostasis activity was used. The peptide of the Preparation Example of the present invention and the control peptide were dissolved in purified water, treated with 10 μl each at concentrations of 0, 62.5, 125, 250, 500 and 1,000 μg/ml in a v-type 96-well plate, respectively, and then sodium chloride 90 μl of aqueous solution was added thereto. After adding 10 μl of the red blood cell suspension thereto, the mixture was mixed at 300 rpm for 10 minutes and reacted at 4° C. for 2 hours or longer. In addition, the degree of aggregation of blood cells due to the formation of nanofibers of each sample was evaluated by visually checking the degree of precipitation of the red blood cell suspension.

As a result, as shown in FIG. 4, it was found that the red blood cell suspension did not precipitate and formed a blood clot at a concentration of 500 μg/ml or more of the peptide of the present invention. This is an effect caused by the aggregation of red blood cells due to the nanofibers formed by the peptide of the present invention, and it was confirmed that the blood coagulation promoting effect was similar to that of the control peptide sample known to have an aggregation effect on blood cells. Therefore, it was confirmed that the peptide of the present invention or a composition containing the same can be usefully used for hemostasis by inducing aggregation of blood cells.

Experimental Example 5

Confirmation of Blood Coagulation Effect of Peptide of the Present Invention (Blood Coagulation Test)

In order to confirm whether the peptide of the present invention has an effect of inducing blood coagulation, blood collected from rat was treated with the peptide of the present invention, and then the coagulation of the blood was confirmed.

First, the clotting time of blood according to the treatment of the peptide of the present invention was evaluated. In a state where the coagulation reaction of the collected rat blood was suppressed in a heparinized vacuum collection tube, 300 μl of blood was transferred to an EP tube, and 150 μl of a solution in which the peptide of the present invention was dissolved in purified water was treated thereto. The clotting time was measured by inverting the tube at 10-second intervals and visually evaluating the flowability of the blood. As a control group, the RADA16 peptide sample and Greenplast (Greenplast Q, GC Green Cross) were used to conduct the experiment in the same manner as the peptide of the present invention.

As a result, as can be seen in Table 2 and FIG. 5 below, when the peptide of Preparation Example was treated at a concentration of 2.5%, it was confirmed that blood clotted after 13 seconds. It took less than 20 seconds for blood to coagulate when treated with Greenplast, and less than 30 seconds when treated with RADA16 peptide. Therefore, it was confirmed that the peptide of the present invention exhibits blood coagulation efficacy similar to or superior to commercially available agents previously used as hemostatic agents.

TABLE 2

|  | Blood Clotting time |
| --- | --- |
| Distilled water | — |
| Greenplast Q | <20 sec |
| RADA16 2.5% | <30 sec |
| Peptide of the present invention 2.5% | 13 sec |

In addition, in order to evaluate the coagulation efficacy of the peptide of the present invention, the peptide of the Preparation Example was treated with rat blood, and its optical density was measured. Specifically, in a state where the coagulation reaction of the collected rat blood was suppressed in a heparinized vacuum collection tube, 300 µl of blood was transferred to a 15 ml conical tube, and 300 µl of the peptide of the present invention solution was added thereto and mixed gently. Then, 30 µl of 0.2 M CaCl$_2$ solution was added thereto and incubated at 37° C. for 10 minutes to accelerate the coagulation reaction. Then, 10 ml of distilled water was carefully added thereto, and 200 µl of the uniformly dispersed supernatant was added to a 96-well plate, and the optical density was measured at a wavelength of 540 nm using a spectrophotometer. Likewise, Greenplast and RADA16 peptide preparations were used as controls.

As a result, as can be seen in FIG. 6, the optical density measured when the peptide of the present invention was treated was 0.41 based on the degree of blood coagulation of the negative control group treated with distilled water, indicating the amount of blood cells in the supernatant was significantly reduced. This shows a better blood coagulation effect than the effect (0.7) when treated with the RADA16 peptide preparation, which is a hemostatic agent that has been commercially available. Accordingly, it was confirmed that the peptide of the present invention and the composition containing the peptide can be usefully used for promoting blood coagulation.

Experimental Example 6

Animal Experiments on the Hemostasis Effect of Peptides of the Present Invention (In Vivo Test)

Animal experiments were conducted to confirm whether the blood coagulation effect of the peptide of the present invention also appeared in real animals. Specifically, an artery was exposed by incising the thigh of an 8-week-old female rat (SD-rat), and then the exposed artery was damaged with a 21 G needle to construct a bleeding model. And, immediately after bleeding, 200 µl of samples prepared by dissolving the peptide of the present invention in purified water at concentrations of 1% and 2. 5%, respectively, were treated on the bleeding site, respectively, and then bleeding blood was absorbed with pre-weighed gauze. After measuring the time required for the bleeding to stop, the amount of blood loss was confirmed by measuring the weight of the gauze in which the blood was absorbed. Greenplast preparation was used as a positive control group, and in the case of a negative control group that was not treated with anything, the experiment was stopped 90 seconds after bleeding started, and the amount of blood loss up to that point was checked.

Figure 7:
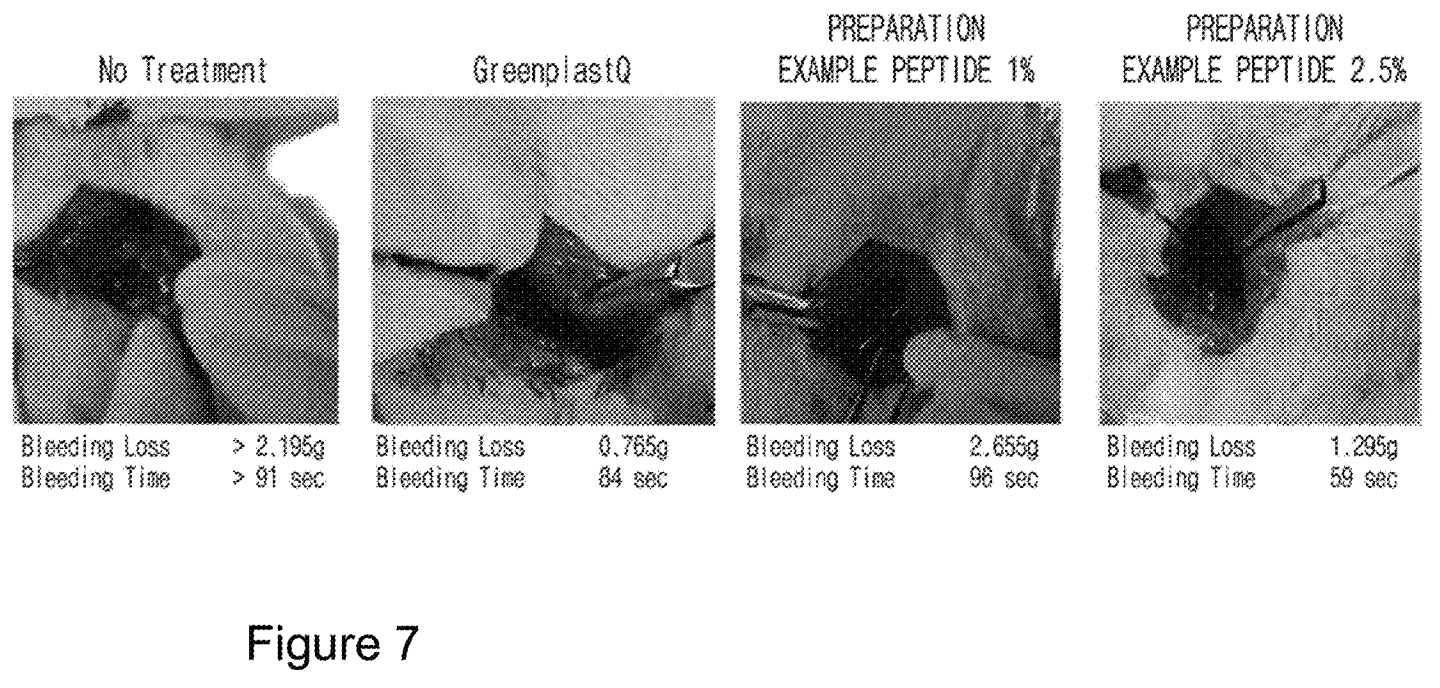

As a result, as can be seen in FIGS. 7 to 9, when the peptide of the present invention was treated, it was found that the hemostasis effect was seen as the bleeding of the rats stopped. In the case of treatment 1% peptide, bleeding stopped after 96 seconds, and in the case of treatment with 2.5% peptide, hemostasis occurred after 59 seconds. Therefore, it was confirmed that there was a similar or superior hemostasis effect compared to the hemostasis time (84 seconds) of the positive control group treated with Greenplast. Even when comparing the amount of blood loss, when 2.5% of the peptide of the present invention was treated, the amount of blood loss was significantly reduced compared to the negative control group in which bleeding occurred for 90 seconds without any treatment. Therefore, it was confirmed that the peptide of the present invention showed a hemostasis effect even when treated to an animal that actually suffered bleeding, and could show an effect similar to that of commercially available hemostatic agents.

Experimental Example 7

Confirmation of Occurrence of Hemolysis by Peptide of the Present Invention (Hemolysis Test)

Furthermore, it was confirmed whether hemolysis, in which blood cells are destroyed, occurs by treatment with the peptide of the present invention. In a state where the coagulation reaction of the collected rat blood was suppressed in a heparinized vacuum collection tube, it was transferred to an EP tube and centrifuged at 1,500 g for 10 minutes. After removing the supernatant plasma, the precipitated red blood cells were treated with 200 µl of 2.5% and 5% of the peptide of the present invention, respectively. A sample treated with 1% SDS was used as a positive control for hemolysis. Each sample was stored for 1 hour in a 37° C. incubator, and then centrifuged again at 1,500 g for 10 minutes. 200 µl of the supernatant was transferred to a 96-well plate, and the optical density was measured at a wavelength of 540 nm.

As a result, as can be seen in FIG. 10, hemolysis occurred in the SDS-treated group, but the peptide of the present invention did not induce hemolysis at both 2.5% and 5% concentrations, as in the negative control group. Therefore, since the peptide of the present invention does not destroy blood cells, it can be confirmed that there is no problem even when used for the purpose of inducing blood coagulation, and that a composition containing the peptide can be usefully used for hemostasis.

In the above, the present invention has been described in detail only for the described embodiments, but it is obvious to those skilled in the art that various changes and modifications are possible within the scope of the technical idea of the present invention, and it is natural that these changes and modifications fall within the scope of the appended claims.

The invention claimed is:

1. A peptide having pH-dependent gelation property, which comprises the amino acid sequence of SEQ ID NO: 1.

2. The peptide according to claim 1, wherein the peptide gelates at pH 4 to pH 8.

3. The peptide according to claim 1, wherein the peptide can induce blood coagulation.

4. A composition for inducing hemostasis, comprising the peptide of claim 1.

5. The composition for inducing hemostasis according to claim 4, wherein the peptide is contained in the composition at a concentration of 0.5 mg/ml to 50 mg/ml.

6. The composition for inducing hemostasis according to claim 4, wherein the composition further comprises calcium ions.

7. The composition for inducing hemostasis according to claim 4, wherein the composition coagulates blood at pH 4 to pH 8.

8. The composition for inducing hemostasis according to claim 4, wherein the composition coagulates blood under the condition that the salt concentration is 50 mM or more.

9. The composition for inducing hemostasis according to claim 4, wherein the composition does not cause hemolysis.

10. The composition for inducing hemostasis according to claim 4, wherein the composition is in the form of at least one selected from the group consisting of powder formulations, patches, gauze, sprays and injections.

11. A method for hemostasis comprising the step of treating the composition of claim 4 to a bleeding site of an animal in which bleeding occurs.

* * * * *